United States Patent
Saied et al.

(10) Patent No.: US 6,949,071 B1
(45) Date of Patent: Sep. 27, 2005

(54) METHOD FOR EXPLORING AND DISPLAYING TISSUE OF HUMAN OR ANIMAL ORIGIN FROM A HIGH FREQUENCY ULTRASOUND PROBE

(75) Inventors: Amena Saied, Paris (FR); Geneviève Berger, Bourg-la-Reine (FR); Pascal Laugier, Paris (FR); Michel Puech, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/600,073

(22) PCT Filed: Jan. 12, 1999
(Under 37 CFR 1.47)

(86) PCT No.: PCT/FR99/00040
§ 371 (c)(1),
(2), (4) Date: Feb. 5, 2001

(87) PCT Pub. No.: WO99/34733
PCT Pub. Date: Jul. 15, 1999

(30) Foreign Application Priority Data
Jan. 12, 1998 (FR) .................................. 98 00209

(51) Int. Cl.⁷ .............................................. A61B 8/00
(52) U.S. Cl. .................................................. 600/445
(58) Field of Search ............................... 600/437–438, 600/443–450, 459, 460; 128/916

(56) References Cited

U.S. PATENT DOCUMENTS 4,167,180 A * 9/1979 Kossoff ....................... 600/445
5,165,415 A * 11/1992 Wallace et al. ............. 600/452
5,293,871 A * 3/1994 Reinstein et al. ........... 600/442
5,551,432 A * 9/1996 Iezzi ........................... 600/445
6,055,452 A * 4/2000 Pearlman .................... 600/547
6,059,728 A * 5/2000 Ritter ......................... 600/443
6,159,153 A * 12/2000 Dubberstein et al. ....... 128/916
6,312,381 B1 * 11/2001 Knell et al. ................. 600/437
6,352,507 B1 * 3/2002 Torp et al. .................. 600/438

OTHER PUBLICATIONS

Foster, F.S., et al., "Ultrasound Backscatter Microscopy of the Eye In Vivo," *1990 Ultrasonics Symposium, Proceedings*, Dec. 4-7, 1990, vol. 3, pp. 1481-1484.

C. Passman and H. Ermert, "Adaptive 150 MHz Ultrasound Imaging of the Skin and the Eye Using an Optimal Combination of Short Pulse Mode and Pulse Compression Mode," *1995 IEEE Ultrasonics Symposium, 1995*, pp. 1291-1294.

Lizzi, F.L., et al., "Ultrasonic Therapy and Imaging in Ophthalmology," *Acoustical Imaging*, vol. 14, pp. 1-15, 1985.

* cited by examiner

*Primary Examiner*—Francis J. Jaworski
(74) *Attorney, Agent, or Firm*—Connolly Bove Lodge & Hutz LLP

(57) ABSTRACT

A method for displaying scanned ultrasound images of tissue employs an apparatus including an ultrasound probe mounted to a mechanical head. A three-dimensional positioning system mounts the head for positioning the probe in proximate orthogonal relation to the tissue. A computer controls the three-dimensional positioning system thereby moving the probe during a scan. The probe transmits high frequency ultrasound waves whose nominal frequency is included within the range from 30 to 100 MHz and with a large pass band, adapted to frequencies reflected by the tissue. The beams of ultrasound transmission are focused in a given zone of the tissue over a vertical penetration distance of between 20 and 30 mm. Reflected signals are acquired and processed for display.

11 Claims, 4 Drawing Sheets

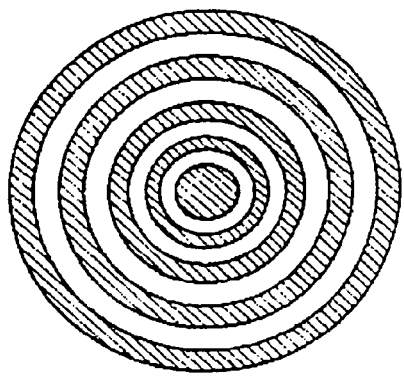
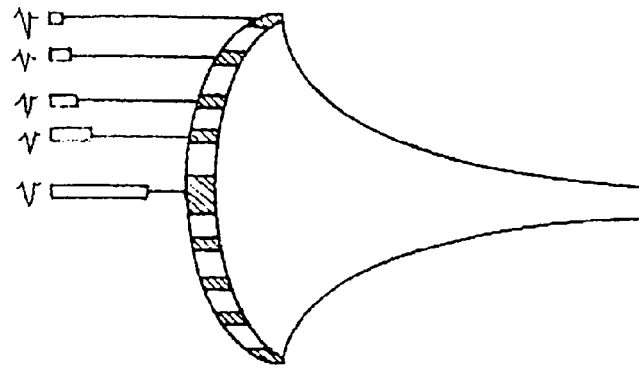
FIG.4a                FIG.4b
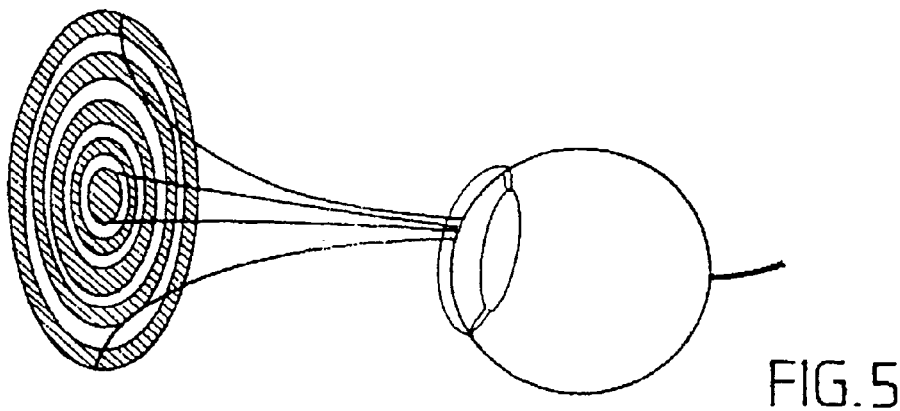
FIG.5
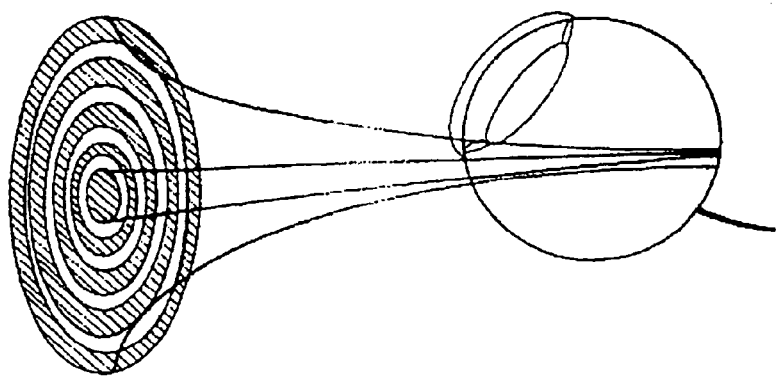
FIG.6

METHOD FOR EXPLORING AND DISPLAYING TISSUE OF HUMAN OR ANIMAL ORIGIN FROM A HIGH FREQUENCY ULTRASOUND PROBE

This application is a 371 of PCT/FR99/00040 filed Jan. 12, 1999.

FIELD OF THE INVENTION

The present invention relates to a process for the investigation and display, using ultrasound echography techniques, of tissue structures of human or animal origin such as in particular the ocular globes and more particularly of the posterior segment (the vitreous cavity, the posterior wall of the globe lined by the choroid and the retina, the macula), tissue structures of the anterior segment (the cornea, the anterior chamber, the iris and the crystalline lens). The invention also relates to a device and an ultrasound probe which allow this investigation and this display to be achieved in 2D or 3D.

BACKGROUND OF THE INVENTION

In ultrasound imaging and more particularly in medical echography, the choice of frequency is dictated by the compromise between resolution and penetration depth. Specifically, because of the increase in attenuation of ultrasound waves with frequency, the penetration depth of ultrasound increases with decreasing frequency. However, the image resolution decreases with decreasing frequency.

In addition, a process for the investigation and display of human tissues is known, through document U.S. Pat. No. 5,178,148, for determining the volume of a tumour or of a gland using signals coming from a probe steered by the process.

Processes are known, in particular through patent FR 2,620,327, for the investigation of ocular structures, by echography, using probes operating at low frequencies of the order of 10 MHz, and focused to a depth roughly equal to the size of an ocular globe (about 23 to 25 mm). These processes mean, on one hand, that images in section of the posterior segment of the eye can be achieved with spatial resolutions of the order of a millimeter and, on the other hand, that a very rough examination of the entire anterior segment of the eye can be carried out.

The major drawback of low-frequency echography is mainly the low resolution (600 to 700 µm) provided by these low frequencies, which do not allow detailed analysis of the retina and the other layers of the posterior wall of the eye (choroid and sclera) and more particularly in the macular region.

In order to increase both the lateral and axial resolution, investigation and display processes using ultrasound probes at high frequency, of the order of 50 to 100 MHz (cf. U.S. Pat. No. 5,551,432 and C. J. PAVLIN, M. D. SHERAR, F. S. FOSTER: "Subsurface ultrasound microscopic imaging of the intact eye", Ophthalmology 97: 244, 1990), with a short focal length (of about 4 to 8 mm), have enabled the use, with a resolution of 50 µm, of structures of the anterior segment of the eye, to depths of the order of 5 mm, or of structures of the peripheral retina which are very close to the anterior segment.

In conclusion, it is therefore accepted that the use of high frequencies seems to be limited to investigation of the anterior segment and the peripheral retina, whereas investigation of the deep structures (posterior segment) requires the use of much lower frequencies, while only providing very low spatial resolutions, of a few hundred microns.

BRIEF DESCRIPTION OF THE INVENTION

The present invention aims to alleviate the drawbacks of the known processes of the prior art, by proposing an investigation and display process using a high-frequency ultrasound probe which combines both very high spatial resolution and a field of investigation covering the anterior and posterior segments of the ocular globe.

To this end, the process for the investigation and display of tissues of human or animal origin is characterized in that:
  an ultrasound probe is positioned, said probe being carried by a head steered by means of a three-dimensional positioning system, in particular a system controlled by a computer at right angles to said tissue structure,
  the probe is controlled such that it generates beams of convergent high-frequency ultrasound waves whose nominal frequency is included within the range from 30 to 100 MHz with a broad bandwidth, adapted to the frequencies reflected by the structure investigated, these waves being focused on a given area of tissue structure,
  the tissue structure is scanned by the positioning system steered by the computer, while said computer carries out, in parallel, the acquisition of the signals reflected by the tissue structure,
  various signal processing operations are carried out on the data coming from the scanning, to improve the reproduction of the information and to facilitate the interpretation thereof by the practitioner.

According to another advantageous characteristic of the invention, the probe is excited such that it generates wave beams whose nominal frequency is included within the range from 30 to 100 MHz with a broad bandwidth, adapted to the frequencies reflected by the structure investigated.

According to yet another advantageous characteristic of the invention, the wave beams are focused over a vertical penetration distance of between 20 and 30 mm.

Other characteristics and advantages of the present invention will emerge from the description given hereinbelow, with reference to the appended drawings which illustrate an entirely non-limiting embodiment of the invention. In the figures:

BRIEF DESCRIPTION OF THE FIGURES

FIGS. 4a and 4b illustrate, on one hand, a front view of one embodiment of the ultrasound probe consisting of an annular array whose focus point can be modified electronically and, on the other hand, a side view of this same probe into which a phase difference has been introduced at transmission or at reception between the various rings making up the array;

FIG. 5 is a view illustrating a use of the process forming the subject of the invention for the investigation of the anterior segment of an ocular globe, using a dynamic focusing probe;

FIG. 6 is a view illustrating a use of the process forming the subject of the invention for the investigation of the posterior segment of an ocular globe, using a dynamic focusing probe;

DETAILED DESCRIPTION OF THE INVENTION

Figure 1:
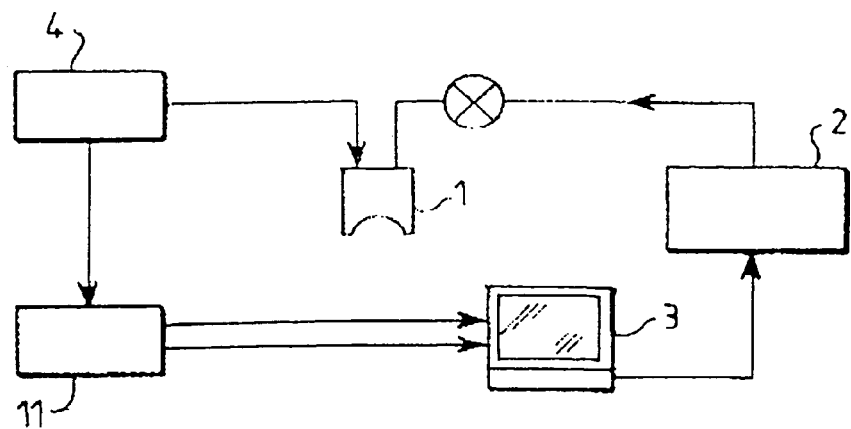
FIG. 1 is a synoptic view of a device enabling the process forming the subject of the invention to be implemented.

According to a preferred embodiment of the process forming the subject of the invention, of which one system enabling its implementation is shown schematically in FIG. 1, the process consists in positioning an ultrasound probe 1 mounted within a head articulated in three dimensions X, Y, Z, at least one direction of which can be fixed, this head being steered by a servo-controlled positioning system 2, controlled by a computer 3, in particular in a direction perpendicular to the medium to be investigated.

This ultrasound probe 1 consists mainly of a transducer, in particular one made of PVDF (polyvinylidene difluoride), controlled by a transmitter/receiver 4, in order to generate beams of convergent, broadband, ultrasonic waves, these waves being able to adopt a spherical or linear profile.

Figures 2, 3:
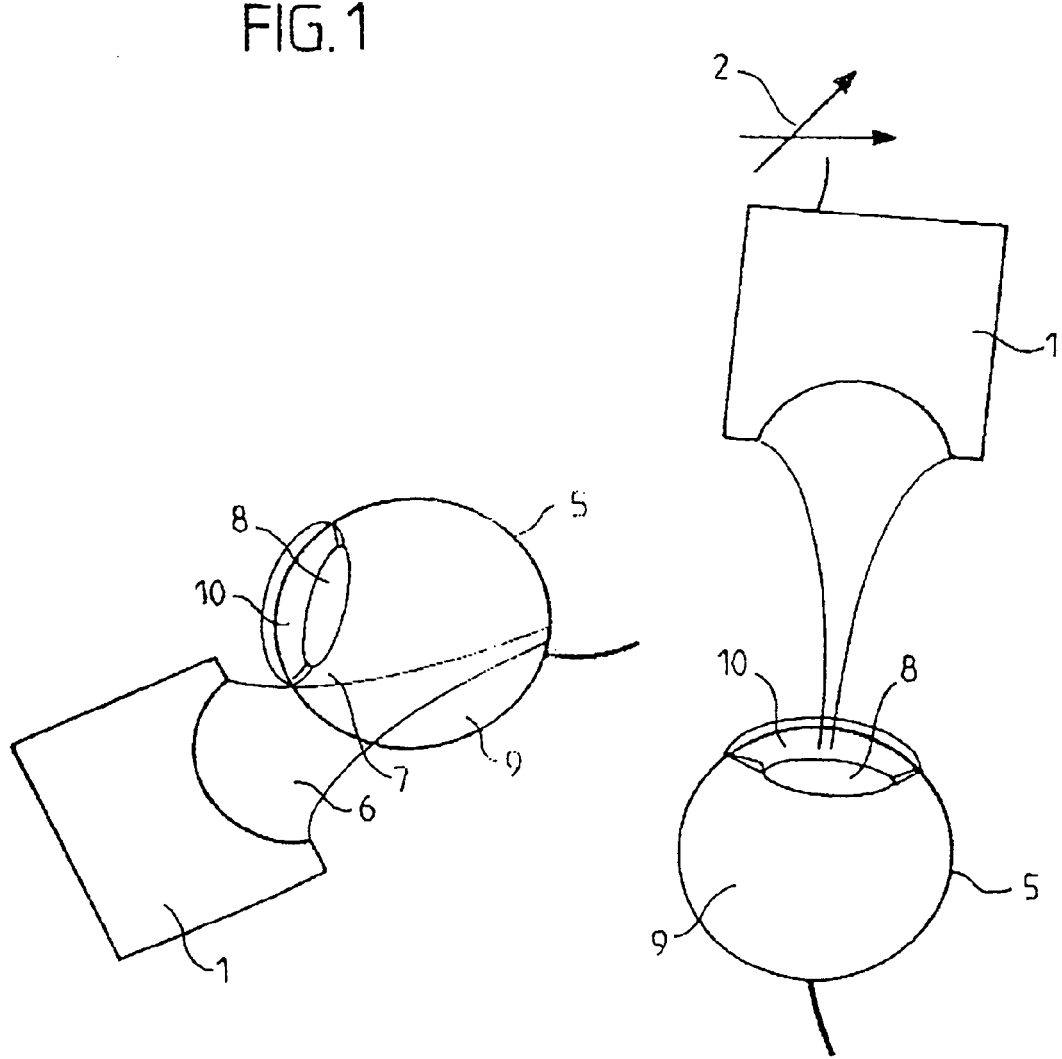
FIG. 2 is a view illustrating a use of the process forming the subject of the invention for the investigation of the posterior segment of an ocular globe.
FIG. 3 is a view illustrating a use of the process forming the subject of the invention for the investigation of the anterior segment of an ocular globe.

Next, FIG. 2 shows an investigation of the posterior segment of an ocular globe 5, previously inserted into a coupling medium 6 which does not impair the propagation of the waves, especially in the retina region. A probe 1 positioned on the pars plana 7 is used to avoid absorption of the ultrasound beam by the lens 8 (this lens also marking the boundary between the posterior segment 9 and the anterior segment 10 of an ocular globe 5). This probe 1 transmits beams of ultrasound waves set within a nominal broadband frequency range varying from 30 to 100 MHz, involving wavelengths going from 50 to 15 am, focused at a focal length or between 70 and 30 mm and preferably 25 mm, corresponding in fact to a focus at an average depth or an ocular globe.

For example, for a probe with a nominal frequency of 50 MHz, lateral and axial resolutions of 220 and 70 $\mu$m respectively are obtained at the focal length.

The receiving system will have a bandwidth adapted to the frequencies reflected by the structure, these frequencies being lower than the transmitted frequencies because of the attenuation by the medium which is crossed.

In order to investigate the anterior segment (cf. FIG. 3), this same probe 1 is used under the same control conditions as previously, in a position offset on the vertical axis (Z axis) at a distance corresponding in fact to the previous focal length.

According to another embodiment, the focal length, especially on the vertical penetration axis, is not modified by a mechanical servocontrol 2 in the position, but by an electronic or digital device steering the probe and able to modify, by careful command, the focusing area of the probe, in order thus to obtain simultaneously a high resolution image of the anterior segment and of the posterior segment of the eye. This probe, with dynamic focusing carried out by an electronic or digital control process, consists of a multi-element probe, with circular symmetry, made up of several concentric annular transducers evenly spaced over a plane surface or with spherical concavity (refer to FIG. 4a). These transducers are independent of each other and are controlled individually in transmission and in reception by pulses which are offset in time (refer to FIG. 4b which shows dynamic focusing obtained by introducing a phase difference—time delay—into the transmission between the various rings).

In transmission, the generated wavefront is convergent and its curvature is modified according to the distance between the structure investigated and the probe. The peripheral rings transmit first and the excitation of the central ring is the most retarded.

Thus the focal length along the axis of the probe can be varied and is therefore determined by the phase difference or the time delay introduced between the various transducers. The same principle of dynamic focusing is used in reception; the electronic delay is adjusted to the depth of the echoes which arrive at that moment at the probe. In this way the depth of field is increased without in any way degrading the lateral resolution.

A measurement system, of which each of the components (digitizer 11, computer 3, control electronics 2, transmitter/receiver 4, etc.) forming it has a bandwidth compatible with the processing and analysis of the signals originating from the anterior segment and/or of the signals coming from the posterior segment of the eye, enables processing of the signals backscattered by the structure investigated. Thus, the backscattered ultrasound signal is amplified then digitized using the digitizer 11, at a given sampling frequency (in particular of the order of 400 MHz over 8 bits).

This same computer controls the stepper on DC motors in order to move the probe and scan the ultrasound beams over the sample in a defined step along X and along Y in order to allow another measurement point or in an R,$\Omega$ step using a probe support head which allows an arciform scan.

For in vivo measurements and investigations, it is necessary, in order to get round the problem of parasitic movements of the eye in its orbit, to process the signal in real time and to have available an extremely fast and accurate probe movement system.

According to another characteristic, the computer is fitted with a module for processing the image and the radiofrequency signal. This module has programmed software which enables the two quantitative approaches, of 2D and/or 3D biometry and of tissue characterization, to be carried out.

The echographic signal can be shown in real time in the form of a A-scan line or in the form of a 2D image of the B-scan type. The B-scan images can display sections in the various planes parallel to the direction of propagation of the ultrasound (cf. FIGS. 7 and 8). A 2D image of the C-scan type can also be calculated in order to display sections in the plane perpendicular to the direction of propagation of the ultrasound. The C-scan is able to show sections located at different depths of the whole ocular globe.

The calculation and the reconstruction of the 3D image can be carried out using programmed mathematical functions specific to the ultrasound data to be processed.

Thus, provided the propagation speed of the ultrasound in the structures investigated is known, it is possible to determine morphological characteristics of these structures, especially their thickness and/or their volume.

The processing software of the radiofrequency signal enables a frequency analysis of the digitized and recorded backscattered signals to be made in order to calculate quantitative ultrasound parameters for the purpose of tissue characterization. These parameters are in particular the attenuation coefficient in dB/cm.MHz (decibels/cm.megahertz), the overall attenuation coefficient in dB/cm, the backscatter coefficient in dB/cm.MHz and the overall backscatter coefficient in dB/cm.

These parameters can be estimated locally and their values can be shown in the form of images (parametric images).

It is of course possible to add other algorithms for processing the radiofrequency signal and the image, algorithms which could produce quantitative morphological and/or tissue information capable of characterizing the structures of the eye.

The images obtained by this investigation process, both for an ocular globe and the region of the anterior segment and the posterior segment, have a resolution which is improved by a factor of at least two to three compared with that obtained with conventional echographs and are not limited by the transparency of the media investigated as in particular with conventional optical investigation means (biomicroscopy, angiography) whose quality can be affected by the presence of cataracts and haemorrhages.

Figure 7:
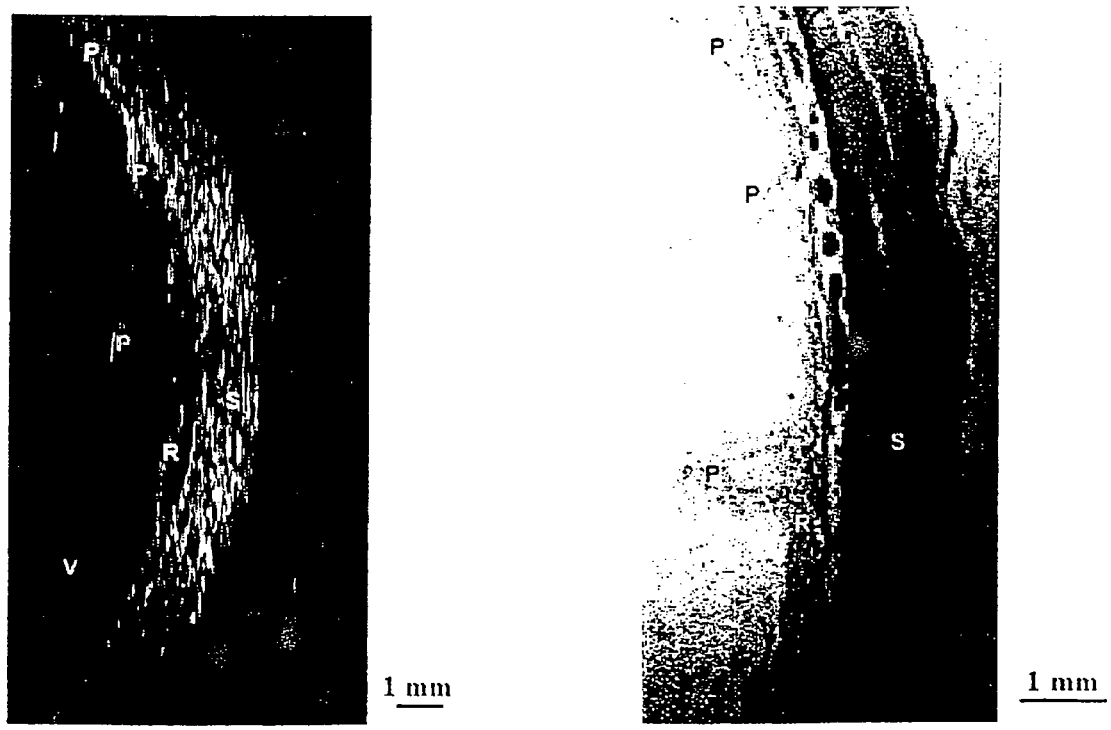
FIG. 7 shows a comparison between a macular section of a human globe in vitro, obtained by macroscopic histological imaging (right side) and an image arising from the process forming the subject of the invention (left side) where P represents the retinal folds, R the retina, S the sclera and V the vitreous humour.
Figure 8:
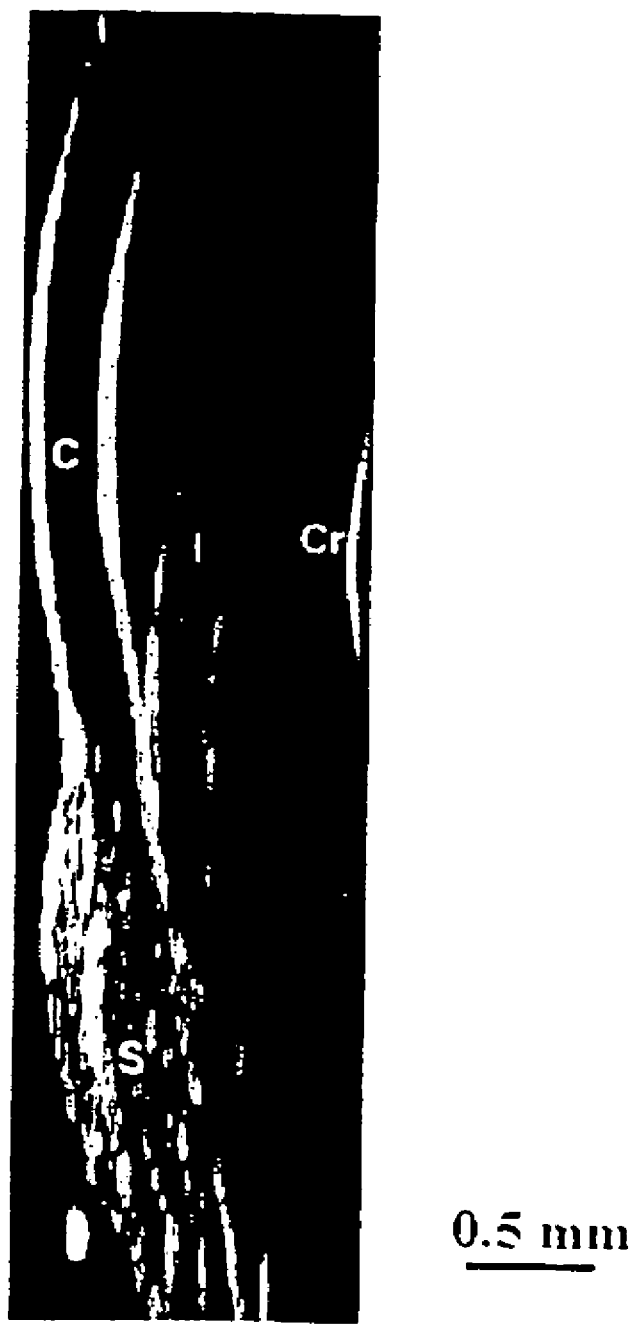
FIG. 8 is the image obtained from an anterior segment of a rabbit's eye, by the process forming the subject of the invention, where C represents the cornea, I the iris, S the sclera and Cr the anterior surface of the lens.

By way of example, FIG. 7 illustrates the similarities between a histological image and an echographic image of the macula of a human eye (in vitro), and FIG. 8 illustrates an image of an anterior segment of a rabbit's eye.

The process and the device which enables its implementation, such as those described previously, are not limited to applications in ophthalmology, but they can also find applications in gynaecology and obstetrics, in gastro-enterology and in the field of cardiovascular examinations and examinations by coelioscopy, or in dermatology and more generally in any medium which reflects a usable signal.

In particular, in the field of dermatology, it is possible, using the investigation and display process forming the subject of the invention, to investigate the various thicknesses of tissue forming the skin. Thus, it is possible for example, by processing the signal, to assess the degree of skin hydration, to evaluate healing of a tissue, to localize and investigate a tumour, and finally, more generally, to to open the way to examining a large number of pathologies currently encountered in dermatology.

The focus point or focusing area of the wave beam will be adjusted within a range going from a few tenths of a millimeter to several millimeters and the waveband used will be between 30 and 100 MHz.

It is of course understood that the present invention is not limited to the embodiments described and shown hereinbefore, but that it encompasses all the variants thereof.

What is claimed is:

1. A method for displaying scanned ultrasound images of tissue, the method comprising the steps:
    mounting an ultrasound probe to a mechanical head;
    connecting the head to a three-dimensional positioning system;
    positioning the probe in proximate orthogonal relation to the tissue;
    controlling the three-dimensional positioning system by a computer for moving the probe during a scan;
    transmitting high frequency ultrasound waves whose nominal frequency is included within the range from 30 to 100 MHz and with a large pass band, adapted to frequencies reflected by the tissue, for combining very high spatial resolution and a field of investigation covering both the anterior and posterior segments of an ocular globe;
    focusing beams of ultrasound transmission in a given zone of the tissue over a vertical penetration distance of between 20 and 30 mm;
    acquiring signals reflected by the tissue during a scan; and
    processing the acquired signals to form an image of the scanned tissue.

2. The process according to claim 1, wherein the tissue to be scanned is in a posterior segment of an ocular globe.

3. The process according to claim 1, wherein the tissue to be scanned is in an anterior segment of an ocular globe.

4. The process according to claim 1, wherein the tissue to be scanned is in a human ocular globe.

5. The process according to claim 1, wherein the tissue to be scanned is investigated during an examination chosen from the group consisting of gynaecology, obstetrics, gastroenterology, cardiovascular, coelioscopy, or dermatology.

6. An apparatus for displaying scanned ultrasound images of tissue structure, the apparatus comprising:
    an ultrasound probe mounted to a mechanical head;
    a three-dimensional positioning system mounting the head thereto for positioning the probe in proximate orthogonal relation to the tissue;
    computer means for controlling the three-dimensional positioning system thereby moving the probe during a scan;
    the probe transmitting high frequency ultrasound waves whose nominal frequency is included within the range from 30 to 100 MHz and with a large pass band, adapted to frequencies reflected by the tissue, for combining very high spatial resolution and a field of investigation covering both the anterior and posterior segments of an ocular globe;
    means for focusing beams of ultrasound transmission in a given zone of the tissue over a vertical penetration distance of between 20 and 30 mm;
    means for acquiring signals reflected by the tissue during a scan; and
    means for processing the acquired signals to form an image of the scanned tissue.

7. The apparatus set forth in claim 6, together with means for electronically modifying a focal distance of the ultrasound probe in order to adjust the focal point of the probe.

8. The apparatus set forth in claim 6, together with a servo-mechanism system for mechanically modifying focal distance of the ultrasound probe.

9. The apparatus set forth in claim 6, wherein the computer means for controlling the three-dimensional positioning system steers stepping motors that permits the probe to generate an arciform scan of the tissue.

10. The apparatus set forth in claim 6, wherein the computer means for controlling the three-dimensional positioning system steers stepping motors that permits the probe to generate a Cartesian scan of the tissue.

11. The apparatus set forth in claim 6, together with coupling means connected at a first end thereof to the probe, an opposite end being opened, for directing the ultrasound waves toward the tissue.

* * * * *